United States Patent [19]

Nakamura et al.

[11] Patent Number: 5,571,729
[45] Date of Patent: Nov. 5, 1996

[54] PROCESS FOR SEPARATING COMPLEX

[75] Inventors: Kenji Nakamura; Taizo Hara; Hideo Katoh; Shinji Satomura, all of Amagasaki, Japan

[73] Assignee: Wako Pure Chemical Industries, Ltd., Osaka, Japan

[21] Appl. No.: 354,264

[22] Filed: Dec. 12, 1994

Related U.S. Application Data

[63] Continuation of Ser. No. 76,777, Jun. 15, 1993, abandoned.

[30] Foreign Application Priority Data

Jun. 17, 1992 [JP] Japan .................................. 4-183018

[51] Int. Cl.$^6$ ...................... G01N 33/538; G01N 33/573
[52] U.S. Cl. ..................... 436/541; 210/656; 210/660; 210/668; 435/7.1; 435/7.4; 436/538; 436/824; 530/412; 530/416; 530/417
[58] Field of Search ...................... 422/59, 70; 435/972, 435/7.1, 7.4, 7.71, 7.9, 7.92; 436/161, 512, 536, 537, 538, 541, 542, 824, 827; 530/341.1, 402, 412, 413, 416, 417; 210/606, 608, 660, 661, 662, 665, 666, 702, 668, 669

[56] References Cited

U.S. PATENT DOCUMENTS

| 5,340,474 | 8/1994 | Kauvar | 210/198.2 |
| 5,352,616 | 10/1994 | Sundrehagan | 436/501 |

FOREIGN PATENT DOCUMENTS

| 0357869 | 3/1990 | European Pat. Off. . |
| 0441470A2 | 8/1991 | European Pat. Off. . |

OTHER PUBLICATIONS

Pierce 1988 Handbook & General Catalog, pp. 128–131 (Rockford, Illinois, 1988).

Fausnaugh et al, "Comparison of Hydrophobic–Interaction and Reversed–Phase Chromatography of Proteins", J. Chromat., 317:141–155 (1984).

Carty et al, "Use of High–Performance Liquid Chromatography for the Purification of Antibodies and Antibody Conjugates and the Study of Antibody–Antigen Interactions", J. Chromat., 442: 279–288 (1988).

Anal. Chem., 1993, 65, 613–616, "Liquid–Phase Binding Assay of Human Chorionic Gonadotropin Using High–Performance Liquid Chromatography", Kenji Nakamura et al.

Primary Examiner—David Saunders
Attorney, Agent, or Firm—Armstrong, Westerman, Hattori, McLeland & Naughton

[57] ABSTRACT

This invention is intended to provide a process by which a complex formed by the interaction between one or more analytes to be measured and affinity substance can be more effectively separated from substances existing together therewith which tend to affect the detection of the complex, for example, free affinity substance, by using high pressure liquid chromatography (HPLC); and a process for measuring a trace component by utilizing said separating process.

This invention is characterized in that a substance which has been modified with a substance capable of changing properties of the complex (a separation-improving substance) and has affinity for the complex is attached to the complex. Because of this characteristic, the invention is effective in that the position of elution of said complex in the HPLC can be freely controlled. Furthermore, it is markedly effective in that the process for measuring a trace component by utilizing the separating process of this invention makes it possible to carry out the measurement with higher precision as compared with conventional measuring processes using HPLC.

13 Claims, 3 Drawing Sheets

PROCESS FOR SEPARATING COMPLEX

This application is a continuation of application Ser. No. 08/076,777 filed Jun. 15, 1993, now abandoned.

BACKGROUND OF THE INVENTION

This invention relates to a process for separating a complex of a trace component in a sample derived from a living body, for example, a body fluid such as serum, blood, plasma or urine, lymphocyte, hemocyte or any of various cells and a substance having a specific affinity for the trace component, from other substances, and a process for measuring the trace component by utilizing said separating process.

It is known that specific substances interact strongly on each other to form a stable complex. The specific substances include, for example, the following combinations: antigen and antibody; protease and its protein protease inhibitor; sugar chain and lectin; enzyme and substrate therefor or coenzyme; physiologically active substance such as hormone, and receptor or transport protein for said active substance; and a pair of polynucleotide chain of duplex DNA.

As processes for measuring a trace component in a sample by utilizing the above interaction, there are the processes previously developed by the present inventors which have been disclosed in Japanese Patent Unexamined Publications Nos. 2-28557, 3-206964 and 3-221865 (EP 0357869-A and EP 0441470-A).

The outline of the process disclosed in Japanese Patent Unexamined Publication No. 2-28557 (EP 357869-A) is given below by taking the case where the interaction between an antigen and an antibody is utilized.

(1) A process for measuring the amount of an analyte in a sample derived from a living body which comprises mixing the sample containing an analyte to be measured with an anti-analyte antibody, which antibody has been labeled with a substance detectable by some method (hereinafter abbreviated as "detectable substance") (labeled antibody); reacting the analyte with the labeled antibody; separating the resulting complex of the analyte (the antigen) and the labeled antibody from free labeled antibody by a high pressure liquid chromatography (HPLC); and measuring the amount of the detectable substance in the complex.

(2) A process for measuring an analyte in a sample derived from a living body which comprises mixing the sample containing an analyte to be measured with the analyte which has a detectable substance attached thereto and an anti-analyte antibody to be measured; reacting the unlabeled analyte and the labeled analyte with the antibody; separating the resulting complex of the analyte (the antigen) labeled with the detectable substance and the antibody from free analyte (antigen) having the detectable substance attached thereto, by a high pressure liquid chromatography (HPLC); and measuring the amount of the detectable substance in the complex or the amount of the detectable substance in the free analyte (antigen) having the detectable substance attached thereto.

The invention disclosed in Japanese Patent Unexamined Publication No. 3-206964 (EP 0441470-A) is a process for measuring "two or more analytes to be measured having the same action and the same detectable chemical characteristics" such as isozymes, hormones different in sugar chain structure, etc.

This process is explained below by taking the case where saliva α-amylase and pancreas α-amylase are analytes to be measured.

This measuring process comprises mixing anti-saliva α-amylase (mouse) monoclonal antibody with a sample containing the above two α-amylases to react the same with saliva α-amylase, separating the resulting complex of saliva α-amylase and anti-saliva α-amylase (mouse) monoclonal antibody from free pancreas α-amylase by HPLC, measuring the amount of saliva α-amylase contained in the complex of saliva α-amylase and anti-saliva α-amylase (mouse) monoclonal antibody and/or the amount of the free pancreas α-amylase, and thereby separating and measuring saliva α-amylase and/or pancreas α-amylase in the sample.

The invention disclosed in Japanese Patent Unexamined Publication No. 3-221865 (EP 0441470-A) is a process for measuring "two or more analytes to be measured having the same action" such as isozymes and hormones different in sugar chain structure, or "two or more analytes to be measured having different actions in spite of their similar structures" such as steroid hormones, human chorionic gonadotropin.

This process is explained below by taking the case where hCG derived from placental villi and hCG derived from choriocarcinoma are analytes to be measured.

This measuring process comprises mixing a sample containing the above two hCG's with anti-hCG-β chain monoclonal antibody having affinity for both hCG's which has been labeled with a detectable substance, and a lectin which has affinity only for hCG derived from choriocarcinoma and does not bind to hCG derived from placental villi; reacting the hCG's with the labeled monoclonal antibody and the lectin; separating the resulting complex of hCG derived from placental villi and the anti-hCG-β chain monoclonal antibody labeled with the detectable substance, the resulting complex of hCG derived from choriocarcinoma, the anti-hCG-β chain monoclonal antibody labeled with the detectable substance and the lectin, and free anti-hCG-β chain monoclonal antibody labeled with the detectable substance, from one another by HPLC; measuring the amount of the detectable substance in each complex; and thereby measuring the amounts of the two hCG's in the sample.

As is clear from the above, the measuring processes disclosed in the above references are characterized in that a complex (or a complex labeled with a detectable substance) formed by the interaction between an analyte to be measured (or an analyte to be measured which has been labeled with the detectable substance) and a substance having affinity therefor (hereinafter abbreviated as "affinity substance") is separated from free affinity substance (or free analyte labeled with the detectable substance) by using HPLC. These processes make it possible to determine the amount of a trace component more easily in a shorter time with much higher precision as compared with conventional measuring processes according to EIA (enzyme immunoassay), RIA (radioimmunoassay), FIA (fluoroimmunoassay) or the like. Therefore, they are thought to be measuring processes of great promise.

In addition, the above references disclose, for example, a process using two or more affinity substances (specifically, two or more affinity substances capable of binding to different sites, respectively, on an analyte to be measured) in the formation of a complex; a process using two or more affinity substances labeled with a detectable substance; the fact that employment of two or more of such affinity substances results in an increased molecular weight of the complex, a higher degree of change of the isoelectric point of the complex, etc. and hence further facilitates the separation of the complex from free affinity substances, so that the precision of measurement can be improved; and the fact that the measuring sensitivity can be increased by labeling each affinity substance with a detectable substance previously.

However, the processes using the two affinity substances (including labeled affinity substances) cannot be utilized when an analyte to be measured has only one site to which the affinity substances can bind. Said processes can cause the phenomenon that properties (molecular weight, hydrophobicity, ionicity, etc.) of the complex are consequently changed, resulting in a shifted position of elution of the complex. But they have been unable to control the above properties of the complex freely.

Therefore, when the two affinity substances are merely used in the separation using HPLC in the above-mentioned processes, the following problems, for example, are caused in some cases. The separation of the complex (or the complex labeled with a detectable substance) from free affinity substance (or free analyte labeled with the detectable substance) is not sufficient, or the position of elution of the complex (or the complex labeled with the detectable substance) is the same as that of a living body component in serum or urine, so that the precision of measurement is lowered. Accordingly, there has been a desire to seek further improvement in said processes.

SUMMARY OF THE INVENTION

This invention was made in consideration of such conditions and is intended to provide a process in which when a complex formed by the interaction between one or more analytes to be measured and an affinity substance is separated by HPLC from substances existing together therewith which tend to affect the detection of the complex, for example, free affinity substance, the complex can be more effectively separated from the free affinity substance and the like; and a process for measuring a trace component by utilizing said separating process.

This invention provides a process for separating a complex of one or more analytes to be measured and a substance having affinity for the analytes (hereinafter abbreviated as "affinity substance A") which comprises combining the complex with a substance which has been modified with a substance capable of changing properties of the complex (hereinafter abbreviated as "separation-improving substance") and has affinity for the complex (hereinafter abbreviated as "modified affinity substance"); and separating the thus treated complex from free affinity substance A (or free analyte(s)) by HPLC on the basis of properties of the separation-improving substance.

This invention further provides a process for measuring an analyte by utilizing the reaction of one or more analytes to be measured with an affinity substance A which comprises combining a complex of the analyte(s) and the affinity substance which is formed by said reaction, with a substance modified with a separation-improving substance and having affinity for the complex, separating the thus treated complex from free affinity substance A (or free analyte(s)) by HPLC on the basis of properties of the separation-improving substance; measuring the amount of this complex or the free affinity substance A (or the free analyte(s)); and then determining the amount of the analyte on the basis of the result of this measurement.

BRIEF DESCRIPTION OF THE DRAWINGS

FIG. 5A shows an elution pattern obtained by analyzing a solution prepared by diluting hemolysate in 10 times with 50 mM phosphate buffer (pH 7.5, containing 150 mM sodium chloride). FIG. 5B shows an elution pattern obtained by analyzing a mixed solution of antibody solution 1, an AFP sample solution, hemolysate and the phosphate buffer. FIG. 5C shows an elution pattern obtained by analyzing a mixed solution of antibody solution 1, an AFP sample solution, hemolysate and antibody solution 2.

DESCRIPTION OF THE PREFERRED EMBODIMENTS

Figure 1:
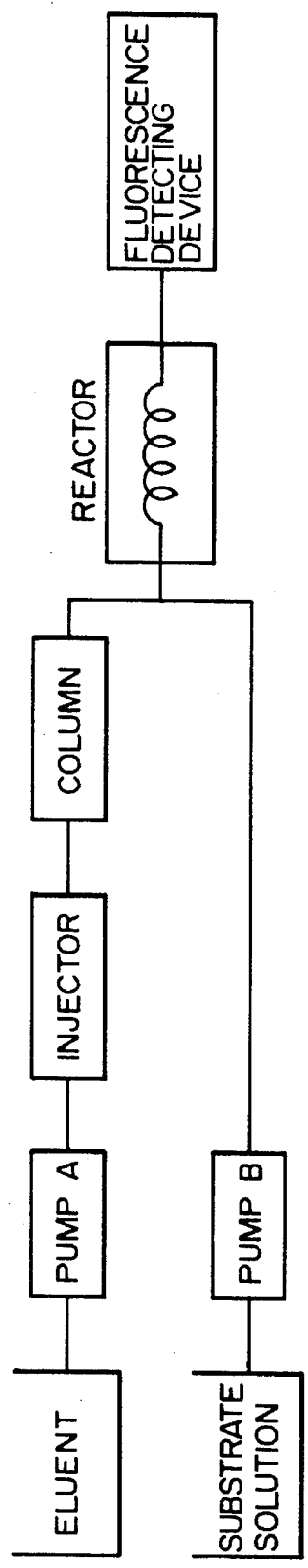
FIG. 1 is a schematic diagram showing the outline of HPLC system used in Example 1.

The present inventors earnestly investigated a process in which when a complex formed by the interaction between one or more analytes to be measured and an affinity substance A is separated by HPLC from substances existing together therewith which tend to affect the detection of the complex, for example, free affinity substance A (or free analyte(s); the analyte may be one which has been labeled with a detectable substance), the complex can be more clearly separated from the free affinity substance A and the like. Consequently, the present inventors found that when a separation-improving substance having suitable properties is attached to said complex and the thus treated complex is separated from the substances existing together therewith which tend to affect the detection of the complex, for example, the free affinity substance A (or the free analyte(s)), on the basis of the properties of the separation-improving substance, it becomes possible to control the position of elution of the complex freely by proper choice of the separation-improving substance, namely, the complex can be more clearly separated from the free affinity substance A and the like by attaching a proper separation-improving substance to the complex. Thus, this invention has been accomplished.

The separation-improving substance used in the separating process of this invention is not critical so long as it can change properties such as molecular weight, hydrophobicity, isoelectric point, etc. of the complex of the analyte(s) and the affinity substance A. Preferable specific examples of the separation-improving substance are proteins (e.g. α-chymotrypsinogen, β-galactosidase, lysozyme, cytochrome c, trypsin inhibitors, etc.), peptides comprising amino acids such as phenylalanine, proline, arginine, lysine, aspartic acid, glutamic acid, etc., halogen atoms (e.g. bromine, chlorine, iodine, etc.), synthetic polymers (e.g. polyethylene glycol, etc.), poly(amino acid) [e.g. poly(glutamic acid)s, poly(aspartic acid)s, polylysines, polyarginines, polyphenylalanines, polytyrosines, etc.], alkyl chains having 3 to 10 carbon atoms, fatty acids (e.g. palmitic acid, oleic acid, stearic acid, etc.), and chemical substances which have a reactive group capable of binding to a substance having affinity for the complex of the analyte(s) and the affinity substance A and have hydrophobicity or ionicity [e.g. N-(ε-maleimidocaproyloxy)succinimide (hereinafter abbreviated as EMCS), N-succinimidyl-6-maleimidohexanoate, bismaleimidohexane (hereinafter abbreviated as BMH), octylamine, etc.].

The substance having affinity for the complex of the analyte(s) and the affinity substance A (hereinafter abbreviated as "affinity substance B") which is used for preparing the modified affinity substance used in this invention is not critical so long as it does not inhibit a reaction for forming a complex with aforesaid complex or free affinity substance A and a reaction for detecting this complex or the free affinity substance A and it has affinity for the analyte(s), the affinity substance A or the complex of them, or affinity for a labeling substance attached to the analyte(s) or the affinity substance A. Preferable specific examples of the affinity substance B are substances having affinity for the analyte(s), for example, antibodies and lectins such as concanavalin A, Lens culinaris lectin, Phaseolus vulgaris lectin, Datura stramonium lectin, Triticum vulgaris lectin, etc. (which bind to a site different from that for the affinity substance A), and substances having affinity for the affinity substance A or said labeling substance, for example, antibodies and lectins such as concanavalin A, Lens culinaris lectin, Phaseolus vulgaris lectin, Datura stramonium lectin, Triticum vulgaris lectin, etc.

As a method for combining the affinity substance B and the separation-improving substance which are used in this invention, there can be exemplified a method of linking a specific reactive group of the affinity substance B to a specific reactive group of the separation-improving substance, a method of replacing a specific reactive group of the affinity substance B by the separation-improving substance, and a method of combining the affinity substance B and the separation-improving substance through a substance having affinity for the affinity substance B (e.g. an antibody, lectin, antigen, inhibitor, DNA or the like). More specifically, there can be exemplified all of, for example, 1) per se well-known methods for combining a labeling substance and an antibody which are generally employed in conventional enzyme immunoassay (EIA), radioimmuno assay (RIA), fluoroimmuno assay (FIA), etc. (see, for example, Yuichi Yamamura" Ikagaku Jikken Koza Vol. 8" 1st ed., NAKAYAMA-SHOTEN Ltd., 1971; Akira Kawano "Zusetsu Keikokotai" 1st ed., Soft Science, Inc., 1983; and Eiji Ishikawa, Tadashi Kawai and Kiyoshi Miyai "KOSO Men-eki Sokuteiho" 2nd ed., IGAKU-SHOIN Ltd., 982), 2) per se well-known methods for modifying a substance and attaching a labeling substance to a substance (see, for example, Ikuzo Uritani, Kensuke Shimura, Michinori Nakamura and Masaru Funazu "Chemical Modification of Proteins Vols. 1 and 2" 1st ed., GAKKAI-SHUPPAN CENTER Ltd., 1981; Yuji Inada et al. "Polyethylene Glycol-Modified Proteins" Seikagaku Vol. 62, No. 11, pp. 1351–1362, Japanese Biochemical Association, 1990; and George H. K. and Mark M. M. "DNA PROBES" STOCKTON PRESS, 1989). The method for combining the affinity substance B and the separation-improving substance may be carried out according to these methods.

The separating process of this invention can easily be practiced, for example, as follows.

A sample containing one or more analytes to be measured is reacted with an affinity substance A and a modified affinity substance, if necessary, by their addition to and mixing in a suitable buffer solution, to form a complex of the analyte(s), the affinity substance A and the modified affinity substance. Then, the complex is separated from substances existing together therewith such as free affinity substance A by a HPLC using a column packed with a packing chosen depending on properties of the separation-improving substance. Needless to say, in the above separating process, the analyte(s) which have been labeled with a detectable substance may also be present.

The separating process of this invention can be effectively utilized for separating (or purifying) a specific trace component in a sample, and it is particularly effective when utilized in the measurement of said trace component.

Examples of the utilization of this invention for measuring a trace component are described below.

(1) A process for measuring the amount of an analyte by utilizing a noncompetitive reaction (measuring process (1)):

First, a sample derived from a living body which contains an analyte to be measured is reacted with an affinity substance A labeled with a detectable substance, and a modified affinity substance, if necessary, by their addition to and mixing in a suitable buffer solution, to form a complex of the analyte, the affinity substance A and the modified affinity substance. Then, the complex is separated from free affinity substance A by a HPLC using a column packed with a packing chosen depending on properties of the separation-improving substance. Needless to say, in the above separation process, the analyte which has been labeled with a detectable substance may also be present. Subsequently, the amount of the detectable substance contained in the thus separated complex is determined by a measuring method suitable for the property of the detectable substance. Separately, measurement is carried out in the same manner as above by using a sample containing a known concentration of the analyte, and there is prepared a calibration curve showing the relationship between the amount of the analyte and the amount of the detectable substance in the complex. The amount of the analyte corresponding to the amount of the detectable substance in the complex is determined using the calibration curve, whereby the amount of the analyte in the sample can be measured.

Although the concentration of the affinity substance A used for forming the complex in the above reaction is varied depending on a value at which the limit of measurement of the analyte is set, it is usually preferable that the affinity substance A is present in the reaction solution at a concentration which is not less than (preferably 2 times or more as high as, more preferably 5 times or more as high as) a concentration at which the affinity substance A can bind to the whole of the analyte of a concentration corresponding to the limit of measurement. Although the concentration of the modified affinity substance to be reacted with the complex is varied depending on a value at which the limit of measurement of the analyte is set, it is usually preferable that the modified affinity substance is present in the reaction solution at a concentration which is not less than (preferably 2 times or more as high as, more preferably 5 times or more as high as) a concentration at which the modified affinity substance can bind to the whole of the analyte of a concentration corresponding to the limit of measurement.

When the affinity substance itself can be measured (detected) by some method, the amount of the analyte in the sample can be determined also by carrying out the above-mentioned reaction by use of an affinity substance A unlabeled with a detectable substance, and determining the amount of the affinity substance A in the resulting complex by a measuring method suitable for properties of the affinity substance A.

(2) A process for measuring the amount of an analyte by utilizing a competitive reaction (measuring process (2)):

First, a sample derived from a living body which contains an analyte to be measured is reacted with the analyte which has been labeled with a detectable substance (hereinafter abbreviated as "labeled analyte"), an affinity substance A, and a modified affinity substance, if necessary, by their addition to and mixing in a suitable buffer solution, to form a complex of the analyte, the affinity substance A and the modified affinity substance, and a complex of the labeled analyte, the affinity substance A and the modified affinity substance (hereinafter abbreviated as "labeled complex"). Then, the labeled complex is separated from the labeled analyte by a HPLC using a column packed with a packing chosen depending on properties of the separation-improving substance. Subsequently, the amount of the detectable substance contained in the thus separated labeled complex is determined by a measuring method suitable for the property of the detectable substance. Separately, measurement is carried out in the same manner as above by using a sample containing a known concentration of the analyte, and there is prepared a calibration curve showing the relationship between the amount of the analyte and the amount of the detectable substance in the labeled complex. The amount of the analyte corresponding to the amount of the detectable substance in the labeled complex is determined using the calibration curve, whereby the amount of the analyte in the sample can be measured.

The concentrations of the affinity substance A and the labeled analyte used for forming the labeled complex in the above reaction are not critical and may be properly determined depending on values at which the limit of measurement of the analyte and the measurement sensitivity for the analyte are set, respectively. However, needless to say, the using concentration of the labeled analyte should be not less than a concentration at which the labeled analyte can bind to the whole of the affinity substance A present in the reaction solution. The concentration of the modified affinity substance used for forming the labeled complex is also not critical and may be properly determined depending on a value at which the limit of measurement of the analyte is set. However, needless to say, the using concentration of the modified affinity substance should be not less than a concentration at which the modified affinity substance can bind to the whole of the complex formed by the reaction of the whole affinity substance A present in the reaction solution with the labeled analyte.

(3) A process for measuring two or more analytes having the same action and the same detectable chemical characteristic (measuring process (3)):

First, a sample derived from a living body which contains analytes to be measured is reacted with a substance having a property of binding specifically to at least one of the analytes but not to at least one of the other analytes (an affinity substance A) and a modified affinity substance having a property of binding to a complex of analyte(s) and the affinity substance A, if necessary, by their addition to and mixing in a suitable buffer solution, to form a complex of specific analyte(s), the affinity substance A and the modified affinity substance. Then, this complex is separated from free analyte(s) by a HPLC using a column packed with a packing chosen depending on properties of the separation-improving substance. Subsequently, the amount of the analyte(s) contained in the thus separated complex or the amount of free analyte(s), or both, are determined by a measuring method suitable for properties of the analyte. Thus, the amount of any of the analytes in the sample can be determined.

The concentration of the affinity substance A used for forming the complex in the above reaction is not critical and may be properly determined depending on values at which the limit of measurement of the analyte and the measurement sensitivity for the analyte are set, respectively. The concentration of the modified affinity substance used for forming the complex is also not critical and may be properly determined depending on a value at which the limit of measurement of the analyte is set. However, needless to say, the using concentration of the modified affinity substance should be not less than a concentration at which the modified affinity substance can bind to the whole of the complex formed by the reaction of the whole affinity substance present in the reaction solution with the analyte(s).

(4) A process for measuring two or more analytes having the same action, or having different actions in spite of their similar structures (measuring process (4)):

First, a sample derived from a living body which contains analytes to be measured is reacted with a substance having affinity for all the analytes and labeled with a detectable substance (an affinity substance A) and a substance having affinity for at least one specific analyte among the aforesaid analytes and modified with a substance capable of changing properties of a complex of analyte(s) and the affinity substance A (a modified affinity substance), if necessary, by their addition to and mixing in a suitable buffer solution, to form a complex of analyte(s) and the affinity substance A (hereinafter abbreviated as "complex A") and a complex of the specific analyte(s), the affinity substance A and the modified affinity substance (hereinafter abbreviated as "complex B"). Then, the complex A, the complex B and free affinity substance A are separated from one another by a HPLC using a column packed with a packing chosen depending on properties of the separation-improving substance. Subsequently, the amount of the detectable substance contained in the separated complex A or the amount of the detectable substance contained in the separated complex B, or both, are determined by a measuring method suitable for the property of the detectable substance. Thus, the amount of any of the analytes in the sample can be determined.

When the affinity substance A itself is measurable (detectable) by some method, the amount of analyte in the sample can be determined also by carrying out the above-mentioned reaction by use of an affinity substance A unlabeled with a detectable substance, and determining the amount of the affinity substance A in the resulting complex by a measuring method suitable for properties of the affinity substance A.

An analyte which can be measured by the measuring process (1) or (2) utilizing the present invention is not critical so long as it satisfies the following condition i) or ii). i) There exists a substance which can form a stable complex with the analyte by a strong interaction between said substance and the analyte, and said substance can be measured (detected) in itself by some method or can be labeled with some detectable substance. ii) The analyte itself can be labeled with some detectable substance, and there exist a substance which can form a stable labeled complex (or a stable complex) with the analyte by a strong interaction between said substance and the analyte. Typical examples of the analyte are proteins, peptides, nucleic acids, sugar chains, lipids, hormones, drugs, etc. which are contained in samples derived from living bodies, for example, body fluids such as serum, blood, plasma, urine and the like, lymphocytes, hemocytes, and various cells. More specific examples of the analyte are tumor markers such as α-fetoprotein (AFP), CA19-9, prostate gland specific antigen (PSA), carcino-embryonic antigen (CEA), substances having special sugar chains which cancerous cells produce, and the like; serum proteins such as immunoglobulin A (IgA), immunoglobul in E (IgE), immunoglobulin G (IgG), β2-microglobulin, albumin, ferritin, and the like; peptides such as C-peptide, angiotensin I, and the like; enzymes such as amylase, alkaline phosphatase, γ-glutamyltransferase (γ-GTP), and the like; antiviral antibodies against clinically noted viruses such as rubella virus, herpesvirus, hepatitis virus, ATL virus, AIDS virus and the like; deoxyribonucleic acid (DNA) and ribonucleic acid (RNA) of pathogens such as viruses and the like, or single-stranded polynucleotides constituting nucleic acids; antigenic substances derived from pathogens such as viruses and the like; antibodies reactive with allergens such as pollen of trees and plants, such as crypomeria, indoor dust and the like; lipids such as lipoproteins and the like; proteases such as trypsin, plasmin, serine protease, and the like; hormones such as insulin, human chorionic gonadotropin (hCG), thyroxine ($T_4$), tri-iodo-thyronine ($T_3$), prolactin, thyroid stimulating hormone (TSH), and the like; drugs such as digoxin, phenytoin, morphine, nicotine, and the like.

The affinity substance A for the analyte which is used in the measuring processes (1) and (2) utilizing this invention is not critical so long as it can form a stable complex with the analyte by a strong interaction between the affinity substance A and the analyte and if necessary, the affinity substance A can be measured (detected) in itself by some method or can be labeled with some measurable (detectable) substance (this does not apply to the case where the analyte itself can be labeled with some detectable substance). The affinity substance A includes, for example, antibodies against substances having antigenicity (including haptens); antigens against antibodies; lectins having affinity for sugar chains having a specific structure, such as concanavalin A, Lens culinaris lectin, Phaseolus vulgaris lectin, Datura stramonium lectin, Triticum vulgaris lectin, and the like; inhibitors for specific enzymes, such as α1-anti-trypsin for trypsin, $\alpha_2$-macroglobulin for plasmin, $\alpha_2$-macroglobulin for serine protease, and the like; and polynucleotide chains complementary to single-stranded polynucleotides which are analytes to be measured.

Analytes which can be measured by the measuring process (3) utilizing this invention are not critical so long as they are per se measurable (detectable) by some method and there exists a substance which can form a stable complex with at least one of the analytes by a strong interaction between the substance and the analyte(s) but does not bind to at least one of the other analytes. Typical examples of the analytes are enzymes and the like which are contained in samples derived from living bodies, for example, body fluids such as serum, blood, plasma, urine and the like, lymphocytes, hemocytes, and various cells. More specific examples of the analytes are enzymes such as amylase, alkaline phosphatase, acid phosphatase, γ-glutamyltransferase (γ-GTP), lipase, creatine kinase (CK), lactate dehydrogenase (LDH), glutamic-oxaloacetic transaminase (GOT), glutamic-pyruvic transaminase (GTP), renin, protein kinases (PK), tyrosine kinase, and the like.

The affinity substance A for the analytes which is used in the measuring process (3) utilizing this invention is not critical so long as it can form a stable complex with at least one of the analytes by a strong interaction between the affinity substance A and the analyte(s) but does not bind to at least one of the other analytes. The affinity substance A includes, for example, antibodies against specific partial structures or antigenic determinants of substances having antigenicity (including haptens); lectins having affinity for sugar chains having a specific structure, such as concanavalin A, Lens culinaris lectin, Phaseolus vulgaris lectin, Datura stramonium lectin, Aleuria aurantia lectin, Ricinus communis lectin, Arachis hypogaea lectin, Triticum vulgaris lectin, and the like; and inhibitors for enzymes, such as amylase, creatine kinase (CK), glutamic-oxaloacetic transaminase (GOT) and the like.

Analytes which can be measured by the measuring process (4) utilizing this invention are not critical so long as they satisfy the following conditions i) and ii). i) There exists a substance which binds to all analytes in the sample and which has in itself a property detectable by some method or can be labeled with a detectable substance. ii) There exists a substance which can form a stable complex with at least one of the analytes by a strong interaction (a high affinity) between the substance and the analyte(s) but does not bind to at least one of the other analytes. Typical examples of the analytes are enzymes, physiologically active substances, tumor associated antigens, substances having a sugar chain, etc. which are contained in samples derived from living bodies, for example, body fluids such as serum, blood, plasma, urine and the like, lymphocytes, hemocytes, and various cells. More specific examples of the analytes are preferably enzymes such as amylase, alkaline phosphatase, acid phosphatase, γ-glutamyltransferase (γ-GTP), lipase, creatine kinase (CK), lactate dehydrogenase (LDH), glutamic-oxaloacetic transaminase (GOT), glutamic-pyruvictransaminase (GTP), renin, protein kinases, tyrosine kinase, and the like; physiologically active substances such as steroid hormones, human chorionic gonadotropin (hCG), prolactin, thyroid stimulating hormone (TSH), luteinizing hormone (LH), and the like; and tumor associated antigens such as prostate gland specific antigen (PSA), α2-macroglobulin, carcino-embryonic antigen (CEA), α-fetoprotein, and the like.

The affinity substance A for the analytes which is used in the measuring process (4) utilizing this invention is not critical so long as it binds to all of the analytes and it has in itself a property detectable by some method or has been labeled with a detectable substance. Specific examples of substance having affinity for all of the analytes which can be used as the affinity substance A or for preparation of the affinity substance A are antibodies against specific partial structures or antigenic determinants of substances having antigenicity (including haptens); lectins having affinity for sugar chains having a specific structure, such as concanavalin A, Lens culinaris lectin, Phaseolus vulgaris lectin, Datura stramonium lectin, Aleuria aurantia lectin, Ricinus communis lectin, Arachis hypogaea lectin, Triticum vulgaris lectin, and the like; and inhibitors for enzymes, such as amylase, creatine kinase (CK), glutamic-oxaloacetic transaminase (GOT), and the like. Preferable specific examples of the affinity substance A are labeled products obtained by labeling these substances with a detectable substance.

The detectable substance used in the measuring processes utilizing the separating process of this invention include, for example, enzymes such as alkaline phosphatase, β-galactosidase, peroxidase, microperoxidase, glucose oxidase, glucose-6-phosphate dehydrogenase, acetylcholineesterase, malate dehydrogenase, luciferase, etc., which are used, for example, in enzyme immunoassay (EIA); radioisotopes such as $^{99m}Tc$, $^{131}I$, $^{125}I$, $^{14}C$, $^3H$, etc., which are used, for example, in radioimmuno assay (RIA); substances which can emit fluorescence, such as fluorescein, dancyl residue, fluorescamine, coumarin, naphthylamine, derivatives thereof, etc., which are used, for example, in fluoroimmunoassay (FIA); luminescent substances such as luciferin, isoluminol, luminol, bis(2,4,6-trifluorophenyl)oxalate, etc.; substances which can absorb an ultraviolet light, such as phenol, naphthol, anthracene, derivatives thereof, etc.; and substances having properties as spin, which are represented by compounds having an oxyl group, such as 4-amino-2,2,6,6-tetramethylpiperidin-1-oxyl, 3-amino-2,2,5,5-tetramethylpyrrolidin-1-oxyl, 2,6-di-t-butyl-α-(3,5-di-t-butyl-4-oxo-2,5-cyclohexadien-1-ylidene)-p-tolyloxyl, etc. Needless to say, the detectable substance is not limited to these substances.

As a method for labeling the affinity substance A with the above-exemplified detectable substance, there can be exemplified all of conventional labeling methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawano "Zusetsu Keikokotai" 1st ed., Soft Science, Inc., 1983; and Eiji Ishikawa, Tadashi Kawai and Kiyoshi Miyai "Koso Men-eki Sokuteiho" 2nd ed., IGAKU-SHOIN Ltd., 1982). The labeling may be carried out according to these methods. Needless to say, the labeling may be carried out by a conventional method utilizing the reaction of avidin (or streptoavidin) with biotin.

As the affinity substance A per se measurable (detectable) by some method which is used in this invention, there can be exemplified substances which themselves have the above-mentioned property as detectable substances, for example, enzymes, substances which can emit fluorescence, luminescent substances, and substances which can absorb an ultraviolet light.

It is sufficient that the separation-improving substance used in this invention is properly chosen in consideration of properties (e.g. pH stability, hydrophobicity, solubility in an aqueous solution, isoelectric point, etc.) of the analyte(s) and the affinity substance A (and/or the affinity substance B).

It is also sufficient that the kind of the packing for the column used in the HPLC is properly chosen depending on properties of the separation-improving substance.

The combination of the packing and the separation-improving substance is explained below in further detail.

① When a packing for gel filtration chromatography is used:

Since packings for gel filtration have a property of separating an objective substance from other substances existing together therewith by utilization of the difference in molecular weight between them, preferable examples of the separation-improving substance are proteins, synthetic polymers such as poly(ethylene glycol)s and the like, and polymeric substances such as poly(amino acid)s and the like. When a modified affinity substance is attached to a complex of one or more analytes to be measured and an affinity substance A, it becomes possible to change the molecular weight of the complex to a desired molecular weight. For attaining a high separating capacity, it is preferable that the molecular weight of the modified affinity substance is 1.2 times or more, preferably 1.5 times or more, more preferably 2 times or more, the molecular weight of the complex.

A separating process on the above principle is advantageous particularly when a sample containing one or more analyte to be measured contains various substances which affect the analysis, for example, serum and these substances are widely different in molecular weight from one another.

To avoid the influence of these substances in such a sample, it is sufficient that the molecular weight of the complex is made larger than the largest of the molecular weights of the substances which affect the analyte. Therefore, it is sufficient that a separation-improving substance having a molecular weight capable of satisfying this condition is chosen and used. When the molecular weight of the complex is controlled by adjustment of the number of molecules of an affinity substance to be attached, as in a conventional method, the affinity substance should be attached to the analyte in a number of (a desired molecular weight/the molecular weight of the affinity substance). Therefore, this method is clearly disadvantageous in that it can be utilized only when a substance having a necessary number of binding sites is an analyte to be measured.

When a separation-improving substance having a molecular weight higher than the cut-off molecular weight of the packing for gel filtration is attached in this invention, the complex containing the analyte(s) is eluted at the void portion of the column. Therefore, the analysis can be achieved in the shortest time. In this case, needless to say, the separation-improving substance need not be a substance having a single molecular weight, namely, the separation-improving substance may be any one so long as it has a molecular weight higher than the cutoff molecular weight of the packing for gel filtration.

The packing for gel filtration includes, for example, YMC-Pack Diol-200 (a trade name, YMC Corp.), YMC-Pack Diol-300 (a trade name, YMC Corp.), and TSK gel (a trade name, Tosoh Corp.)

② When a packing for hydrophobic chromatography is used:

Since packings for hydrophobic chromatography have a property of separating an objective substance from other substances existing together therewith by utilization of the difference in hydrophobicity between them, preferable examples of the separation-improving substance are substances which permit proper adjustment of the hydrophobicity of the complex, for example, highly hydrophobic proteins (e.g. α-chymotrypsinogen, β-galactosidase, etc.), peptides comprising highly hydrophobic amino acids such as phenylalanine, proline, etc., poly(amino acid)s [e.g. poly-(glutamic acid)s, poly (aspartic acid)s, polylysines, polyarginines, polyphenylalanines, polytyrosines, etc.], alkyl chains having 3 to 10 carbon atoms, halogen atoms (e.g. bromine, chlorine, iodine, etc.), highly hydrophobic chemical substances (e.g. octylamine, EMCS, BMH, etc.), and fatty acids (e.g. palmitic acid, oleic acid, stearic acid, etc.).

When a peptide is used as separation-improving substance, it is preferably a peptide comprising one or more highly hydrophobic amino acids, and it is sufficient that the hydrophobicity is adjusted by choosing the chain length of the peptide. In the case of peptides comprising only hydrophobic amino acids and poly(amino acid)s, the number of the amino acids is preferably 2 to 15 because when it is more than 15, the water solubility of the peptides and the poly(amino acid)s is lowered. When separation-improving substance is a halogen atom, the modified affinity substance can easily be obtained by direct halogenation of an affinity substance B, and its hydrophobicity can be properly adjusted by changing the amount of the halogen introduced. As the highly hydrophobic chemical substances, substances having a long alkyl chain can be exemplified besides the above-exemplified substances. The hydrophobicity of such substances can be adjusted by proper choice of the length of the alkyl chain.

Since separation-improving substances having too high a hydrophobicity have a low water solubility, it becomes necessary to use an organic solvent in the combining reaction of the affinity substance B and the separation-improving substance, so that the following problem, for example, is caused in some cases. The resulting modified affinity substance is denatured or has a lowered activity, or it is insoluble in water. Therefore such separation-improving substances are not preferable.

The packing for hydrophobic chromatography includes, for example, Butyl-NPR (a trade name, Tosoh Corp.), Butyl MCI gel (a trade name, Mitsubishi Kasei Corp.), and Phenyl MCI gel (a trade name, Mitsubishi Kasei Corp.).

③ When a packing for ion-exchange chromatography is used:

Since an objective substance is separated from other substances existing together therewith by utilizing the difference in ionicity between them, preferable examples of the separation-improving substance are basic proteins (e.g. lysozyme, cytochrome c, etc.); acidic proteins (e.g. trypsin inhibitors, etc.); peptides comprising residues of basic amino acids such as arginine, lysine, etc. or residues of acidic amino acids such as aspartic acid, glutamic acid, etc.; poly(amino acid)s comprising 50 or more of the above-exemplified amino acid residues; and fatty acids (e.g. palmitic acid, oleic acid, stearic acid, etc.). In general, in ion-exchange chromatography, a high separating capability and a high specificity can be attained when an analyte to be measured is once adsorbed on a column and then eluted. Therefore, when a cationic separation-improving substance is used, a packing for a cation-exchange chromatography is preferably used. When an anionic separation-improving substance is used, a packing for any anion-exchange chromatography is preferably used.

When a peptide comprising only basic amino acid residues (or acidic amino acid residues) or a poly(amino acid) is used as separation-improving substance, the elution time of the complex can be freely controlled by adjusting the number of amino acid residues. When there is used a peptide or a poly(amino acid), which comprises usually 5 or more, preferably 50 or more, more preferably 100 or more amino acid residues, the position of elution of the complex can be completely separated from those of living body components in serum or urine. Therefore, employment of such a peptide or poly(amino acid) is preferable. When the aforesaid peptide or poly(amino acid) is a synthetic peptide or a synthetic poly(amino acid), the length and ionicity of the peptide or poly(amino acid) are proportional to each other. Therefore, the position of elution of the complex can easily be controlled by using as separation-improving substance the peptide or poly(amino acid) which has a length properly adjusted at the time of synthesis.

Also when there exist a plurality of components of serum which affect the measurement, adjustment of the ionicity of the complex to an ionicity higher than that of the components of serum by use of a separation-improving substance is effective in that the time required for the analysis can be reduced by utilizing a stepwise gradient.

Since packings for ion-exchange chromatography generally have a high exchange capacity (absolute adsorption capacity for ionic substance), they can adsorb the whole of a complex having a separation-improving substance attached thereto, even when there is analyzed a sample in which a large absolute amount of ionic substances exist together with one or more analytes to be measured, for example, a sample derived from a living body, such as serum. Therefore, said complex can be eluted at a position at which the influence of these substances can be substantially avoided. In addition, since the separation-improving substances utilizable in the present method have a high water solubility, a complex having any of them attached thereto has a water solubility higher than before the attachment. Therefore, in the present method, the analyte(s) to be measured is hardly denatured or inactivated during the reaction for formation of the complex having the separation-improving substance attached thereto.

The packing for ion-exchange chromatography includes, for example, packings for anion-exchange chromatography, such as DEAE-MCI gel (a trade name, Mitsubishi Kasei Corp.), QAE MCI gel (a trade name, Mitsubishi Kasei Corp.), Wakobeads DEAE gel (a trade name, Wako Pure Chemical Industries Ltd.), etc., and packings for cation-exchange chromatography, such as SP MCI gel (a trade name, Mitsubishi Kasei Corp.), CM MCI gel (a trade name, Mitsubishi Kasei Corp.), Wakobeads CM gel (a trade name, Wako Pure Chemical Industries Ltd.), etc.

Among the above-mentioned chromatography, the use of ion-exchange chromatography is the most preferable. According to the gel filtration chromatography, it is necessary to use a column having a certain length. When the shortening of the separation time is required, it is better to use the ion-exchange chromatography. Further, the gel filtration chromatography is not suitable for separating an analyte having a very high molecular weight (a molecular size of about 1000 Å or more). In the case of the hydrophobic chromatography, when an analyte is a physiologically active substance having a high-order structure such as protein, since a hydrophobic substance is bound to the analyte as a separation-improving substance, the high-order structure is destroyed by the use of an organic solvent to lose the activity of the analyte in the separation procedure. For this reason, it is not desirable to use a substance having high hydrophobicity. Further, the higher the hydrophobicity of the affinity substance B bound to a hydrophobic substance as a separation-improving substance becomes, the lower the water solubility becomes. Therefore, the usable hydrophobic region becomes smaller.

On the other hand, the ion-exchange chromatography can separate the analyte more effectively by applying very fine difference in ionicity. Further, according to the ion-exchange chromatography, since separation-improving substances having various ionicity can be selected optionally, it is possible to separate the analyte under the most stable pH conditions. In addition, since the separation-improving substance per se used in the ion-exchange chromatography has high water-solubility, there is almost no fear of causing a precipitation of analyte even if bound to the analyte, resulting in making possible to carry out the separation under stable conditions.

When an analyte is measured by a measuring process utilizing the separating process of this invention, an objective peak due to the analyte can be shifted to a position at which components of serum, urine or the like have no influence on the measurement. Furthermore, the following effect can also be obtained. The positions of elution of complexes containing various analytes to be measured, respectively, can be made the same by using a proper combination of modified affinity substances, depending on the analytes. Therefore, the various analytes can be measured using HPLC under specific analysis conditions.

In the measuring process utilizing the separating process of this invention, the amount of the detectable substance (or the affinity substance A) contained in each of the complexes (including both of the complexes having or not having the modified affinity substance attached thereto) separated by HPLC is measured by a predetermined method on the basis of the property detectable by some method of the detectable substance (or the affinity substance A). For example, when said property is an enzyme activity, the measurement is carried out according to a conventional method of EIA, for example, the method described in Tsunehiro Kitagawa, Toshio Nanbara, Akio Tsuji, and Eiji Ishikawa "Koso Meneki Sokuteiho", an extra issue No. 31 of Tanpakushitsu Kakusan Koso, pp. 51–63, KYORITSU-SHUPPAN Ltd., published on Sep. 10, 1987, etc. When the detectable substance is a radioisotope, the measurement is carried out according to a conventional method of RIA by properly choosing and using a measuring instrument such as GM counter, liquid scintillation counter, well-type counter, counter for HPLC, or the like, depending on the kind and intensity of a radiation emitted by said radioisotope (see, for example, Yuichi Yamamura "Ikagaku Jikken Koza Vol. 8" 1st ed., NAKAYAMA-SHOTEN Ltd., 1971). When said property is fluorescence-emitting properties, the measurement is carried out according to a conventional method of FIA using a measuring instrument such as fluorometer, for example, the method described in Akira Kawano "Zusetsu Keikokotai" 1st ed., Soft Science Inc., 1983, etc. When said property is luminescence-emitting properties, the measurement is carried out according to a conventional method using a measuring instrument such as photon counter, for example, the method described in Tsunehiro Kitagawa, Toshio Nanbara, Akio Tsuji, and Eiji Ishikawa "Koso Meneki Sokuteiho", an extra issue No. 31 of Tanpakushitsu Kakusan Koso, pp. 252–263, KYORITSU-SHUPPAN Ltd., published on Sep. 10, 1987, etc. When said property is ultraviolet-light-absorbing properties, the measurement is carried out by a conventional method using a measuring instrument such as spectrophotometer. When the detectable substance is a substance having properties as spin, the measurement is carried out according to a conventional method using an electron spin resonance apparatus, for example, the method described in Tsunehiro Kitagawa, Toshio Nanbara, Akio Tsuji, and Eiji Ishikawa "Koso Meneki Sokuteiho", an extra issue No. 31 of Tanpakushitsu Kakusan Koso, pp. 264–271, KYORITSU-SHUPPAN Ltd., published on Sep. 10, 1987, etc.

In the separating process of this invention, the reaction conditions for reacting the analyte(s) with the labeled or unlabeled affinity substance A to form the complex, the reaction conditions for reacting the analyte(s) with labeled analyte(s) and the affinity substance A to form the labeled complex, or the reaction conditions for the combining reaction of each of these complexes with the modified affinity substance, are not critical so long as the reaction conditions inhibit neither the formation of the complex (or the labeled complex) nor the combining reaction of each of these complexes with the modified affinity substance. The reaction is carried out under conditions employed for forming a complex or the like in a conventional method, for example, EIA, RIA, FIA or affinity chromatography. For example, when a buffer solution is used in the reaction, as the buffer and other reagents, those used in the above conventional methods may be properly chosen. Although the pH at the reaction is not critical so long as it inhibits neither the formation of the complex (or the labeled complex) nor the combining reaction of each of these complexes with the modified affinity substance, it is usually 2 to 10, preferably 5 to 9. Although the temperature at the reaction is also not critical so long as it inhibits neither the formation of the complex (or the labeled complex) nor the combining reaction of each of these complexes with the modified affinity substance, it is usually 0°–50° C., preferably 20°–40° C. As to the reaction time, since the time required for the formation of the complex (or the labeled complex) and the combination of each of these complexes and the modified affinity substance varies depending on properties of analytes, the affinity substance A and the modified affinity substance, the reaction may be carried out for several seconds to several hours, depending on their properties.

In the HPLC used for separating the complex (or the labeled complex) [including both of the complexes (or the labeled complexes) having or not having the modified affinity substance attached thereto; hereinafter the same applied] and free affinity substance A in the separating process of this invention, any apparatus can be used without any particular problem so long as it is usually used in the analysis field and has a constant flow rate.

A solvent (an eluent) used for separating the complex (or the labeled complex) and free affinity substance A by the HPLC is not critical so long as it neither decomposes the formed complex (or the formed labeled complex) into analyte(s) and the affinity substance (and modified affinity substance), nor takes the property detectable by some method away from the affinity substance A contained in the complex (or the labeled complex) or away from the detectable substance of affinity substance A. Usually, as the solvent, there is preferably used any of buffer solutions which are used in conventional methods such as EIA, RIA, FIA, affinity chromatography, etc. Preferable specific examples of the solvent are buffer solutions having a pH of 2 to 10 prepared by properly choosing, depending on properties of the complex (the labeled complex) and free affinity Substance A, the following materials, followed by addition and mixing: for example, buffers such as phosphates, acetates, citrates, Good's buffers, tris(hydroxymethyl)aminomethane, and the like; salts such as sodium chloride, potassium chloride, ammonium sulfate, and the like; polar organic solvents such as methanol, ethanol, isopropanol, acetonitrile, tetrahydrofuran, and the like; and surfactants.

In the measuring process utilizing the separating process of this invention, for the measurement after the separation by HPLC, there is preferably employed the method comprising introducing an effluent from a column of HPLC into a detection section as it is, and directly measuring the amount of the detectable substance (or the affinity substance A) contained in the complex (or the labeled complex) in the effluent, which method is described, for example, in Shoji Hara and Akio Tsuji "Newest Liquid Chromatography" 1st ed., pp. 92–104, NANZANDO Ltd., published on Feb. 1, 1978. The reason is that this method permits rapid measurement. In this case, when the property detectable by some method of the affinity substance A or the detectable substance of affinity substance A is, for example, an enzyme activity, a reaction section of so-called post column method, in which a reagent for measuring the enzyme activity is added to the effluent to react therewith, should of course be provided between the column of HPLC and the detection section. As the reagent for measuring the enzyme activity which is used in the reaction section when said property of the detectable substance (or the affinity substance A) is the enzyme activity, there may be used a reagent prepared by a conventional method, for example, a method based on the content of Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 51–63, KYORITSU-SHUPPAN Ltd., published on Sep. 10, 1987, or there may be properly chosen and used a reagent of a commercially available kit for clinical examination. Also when said property of the detectable substance (or the affinity substance A) is other than enzyme activity, a suitable reaction section may be used between the column of HPLC and the detection section in order to add and react a predetermined reagent for the purpose of increasing the detection sensitivity.

When a plurality of eluents different in components from one another are used in the HPLC in the separating process of this invention, either a concentration gradient method (a linear gradient method) or a stepwise method may be employed for carrying out the HPLC, though the stepwise method is preferable because it is advantageous, for example, in that it requires only simple and easy operations, permits reduction of the practical analysis time, and gives a sharp objective peak.

This invention is more concretely explained below with reference to Examples, which are not by way of limitation but by way of illustration.

EXAMPLE 1

Measurement of human chorionic gonadotropin (hCG) and α-fetoprotein (AFP) (by use of β-galactosidase as separation-improving substance and a packing for gel filtration).

Eluent

An eluent was prepared by dissolving 3.9 g of monosodium phosphate, 81 g of disodium phosphate dodecahydrate, and 44 g of sodium chloride in deionized water, adjusting the resulting solution to pH 7.5, and then making up the total volume of 5 liters.

Substrate solution

In 80 ml of the eluent was dissolved 1.66 g of 3-(p-hydroxyphenyl)-propionic acid, and 1N NaOH was added to adjust the resulting solution to pH 7.5, followed by making up the total volume of 100 ml. A 30% aqueous hydrogen peroxide solution was diluted with thus obtained solution, whereby a 20 mM solution of $H_2O_2$ was prepared as a substrate solution.

Antibody solution 1

Anti-hCG-α chain monoclonal antibody (available from Wako Pure Chemical Industries, Ltd.) was treated into Fab' by a conventional method. This Fab' was labeled with horseradish peroxidase (POD) by a conventional method and the thus obtained POD-labeled anti-hCG-α chain-Fab' was added to 50 mM phosphate buffer (pH 7.5, containing 150 mM sodium chloride) to adjust the protein concentration to 3 nM, whereby antibody solution 1 was obtained.

Antibody solution 2

Anti-hCG-β chain monoclonal antibody (available from Wako Pure Chemical Industries, Ltd.) was treated into Fab' by a conventional method. This Fab' was combined with β-galactosidase (β-Gal, mfd. by Oriental Yeast Co., Ltd.) by a conventional method using sulfosuccinimidyl-4-(N-maleimidomethyl)cyclohexane-1 -carboxylate (Sulfo-SMCC) (mfd. by Pierce Chemical Co.). The thus obtained β-Gal-attached anti-hCG-β chain-Fab' was added to 50 mM phosphate buffer (pH 7.5, containing 150 mM sodium chloride) to adjust the protein concentration to 50 nM, whereby antibody solution 2 was obtained.

Antibody solution 3

POD-labeled anti-AFP-Fab' obtained by treating anti-AFP monoclonal antibody (available from Wako Pure Chemical Industries, Ltd.) according to the preparation method of antibody solution 1 was added to 50 mM phosphate buffer (pH 7.5, containing 150 mM sodium chloride) to adjust the protein concentration to 3 nM, whereby antibody solution 3 was obtained.

Antibody solution 4

Anti-AFP monoclonal antibody (available from Wako Pure Chemical Industries, Ltd.) which had been confirmed to be different in epitope from the monoclonal antibody used in antibody solution 3 was treated according to the preparation method of antibody solution 2. The thus obtained β-Gal-attached anti-AFP-Fab' was added to 50 mM phosphate buffer (pH 7.5, containing 150 mM sodium chloride) to adjust the protein concentration to 50 nM, whereby antibody solution 4 was obtained.

hCG sample solution

A hCG sample solution was prepared by adding commercially available hCG (derived from placental villi, available from Sigma Chemical Co.) to 50 mM phosphate buffer (pH 7.5, containing 150 mM sodium chloride) to adjust the hCG concentration to 250 mIU/ml.

AFP sample solution

An AFP sample solution was prepared by adding AFP purified from human placenta (available from Wako Pure Chemical Industries, Ltd.) to 50 mM phosphate buffer (pH 7.5, containing 150 mM sodium chloride) to adjust the AFP concentration to 1 nM.

Use conditions of HPLC

The outline of a system is given in FIG. 1.

Column: 0.8 φ×30 cm.

Packing: YMC Pack Diol-200 (a trade name, YMC Corp.).

Flow rate: the eluent; 1.0 ml/min, the substrate solution; 0.1 ml/min.

Reaction section: 0.025 φ×1,000 cm (maintained at 55° C.).

Detection: Fluorescence was measured at an excitation wavelength of 320 nm and an emission wavelength of 404 nm.

Measuring procedure

Specimens 1 to 5 having the compositions shown in Table 1 were prepared. Each specimen was allowed to stand at 30° C. for 30 minutes and then 50 μl of the specimen was analyzed by HPLC.

TABLE 1

|  | Specimen | | | | |
| --- | --- | --- | --- | --- | --- |
|  | 1 | 2 | 3 | 4 | 5 |
| hCG sample solution | 30 ul | 30 ul | — | — | 30 ul |
| AFP sample solution | — | — | 30 ul | 30 ul | 30 ul |
| Antibody solution 1 | 30 ul | 30 ul | — | — | 30 ul |
| Antibody solution 2 | — | 30 ul | — | — | 30 ul |
| Antibody solution 3 | — | — | 30 ul | 30 ul | 30 ul |
| Antibody solution 4 | — | — | — | 30 ul | — |
| Phosphate* buffer | 30 ul | — | 30 ul | — | — |

*50 mM phosphate buffer (pH 7.5, containing 150 mM NaCl)

Results

As a result of the analysis of the specimens 1 and 2, it was found that the POD-labeled anti-hCG-α chain-Fab' was eluted after 10.5 minutes, a complex of the POD-labeled anti-hCG-α chain-Fab' and hCG (complex-1) after 9.5 minutes, and a complex of the POD-labeled anti-hCG-α chain-Fab', the β-Gal-attached anti-hCG-β chain-Fab' and hCG (complex-2) after 6.8 minutes. As a result of the analysis of the specimens 3 and 4, it was found that the POD-labeled anti-AFP-Fab' was eluted after 10.5 minutes, a complex of the POD-labeled anti-AFP-Fab' and AFP (complex-3) after 9.1 minutes, and a complex of the POD-labeled anti-AFP-Fab', the β-Gal-attached anti-AFP-Fab' and AFP (complex-4) after 6.8 minutes. In the case of the specimen 2 and the specimen 4, complex-1 and complex-3 were not detected, respectively.

From the above results, it can be seen that the employment of the modified affinity substances permits clearer separation of the POD-labeled antibody and the complex from each other, and that the employment makes the elution times of complex-2 and complex-4 the same (both of them were eluted after 6.8 minutes), namely, the employment makes it possible to carry out the analysis by using HPLC under the same conditions even when different analytes are measured.

In the case of the specimen 5, complex-2 was eluted after 6.8 minutes, complex-3 after 9.1 minutes, and the POD-labeled anti-hCG-α chain-Fab' and POD-labeled anti-AFP-Fab' after 10.5 minutes.

As is clear from the above results, proper employment of the modified affinity substances makes it possible to measure different analytes (hCG and AFP) at the same time.

EXAMPLE 2

Measurement of AFP (by use of β-Gal as separation-improving substance and a packing for hydrophobic chromatography).

Eluent A

As eluent A, 50 mM phosphate buffer (pH 7.5) containing 1.7M ammonium sulfate was used.

Eluent B

As eluent B, 50 mM phosphate buffer (pH 7.5) was used.

Substrate solution

The same as in Example 1.

Antibody solution 1

The same as the antibody solution 3 used in Example 1.

Antibody solution 2

The same as the antibody solution 4 used in Example 1.

Sample

The same as the AFP sample solution used in Example 1.

Use conditions of HPLC

Figure 2:
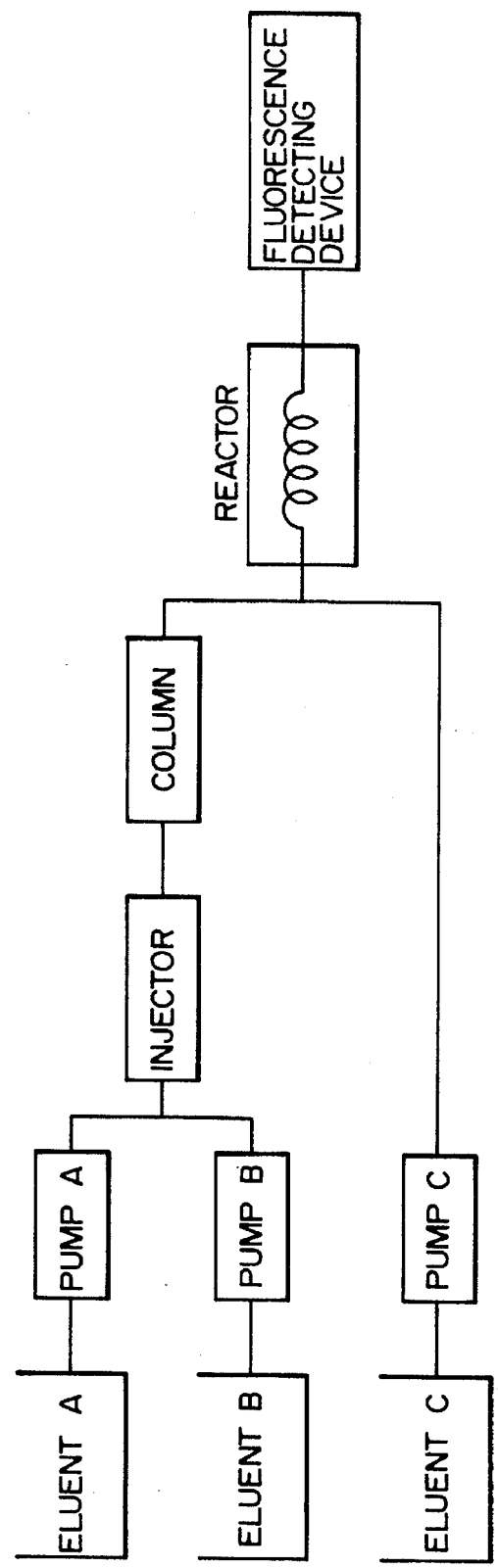
FIG. 2 is a schematic diagram showing the outline of a HPLC system used in Examples 2, 3, 4, 5, 6, 7, 8 and 9.

The outline of a system is given in FIG. 2.

Column: 0.46 φ×2.5 cm.

Packing: Butyl-NPR (a trade name, Tosoh Corp.)

Flow rate: eluents A+B; 1.0 ml/min, the substrate solution; 0.1 ml/min.

Reaction section: 0.025 φ×1,000 cm (maintained at 55° C.).

Detection: Fluorescence was measured at an excitation wavelength of 320 nm and an emission wavelength of 404 nm.

Figure 3:
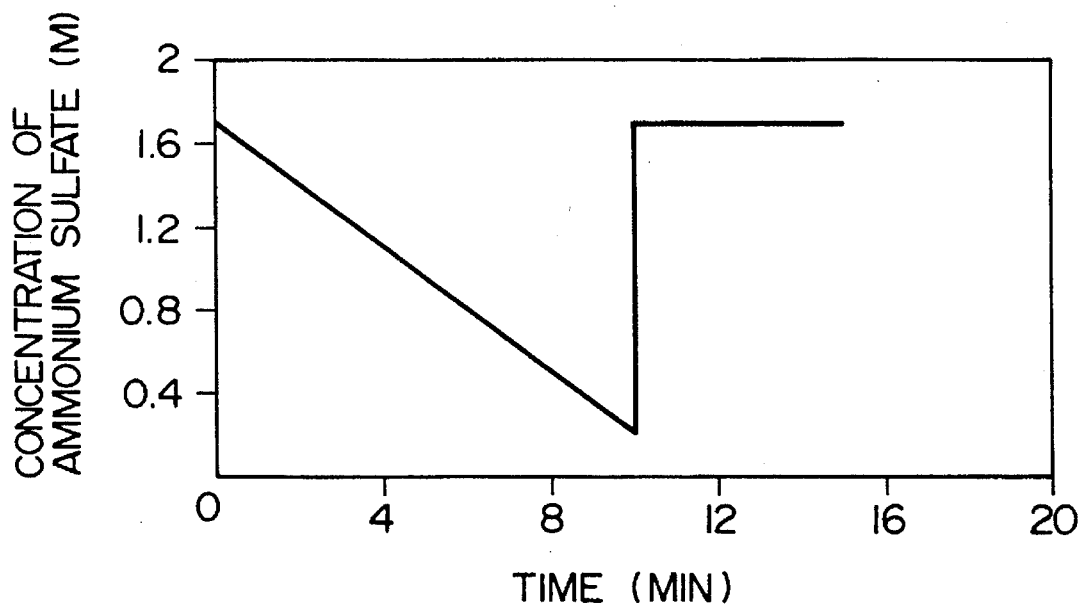
FIG. 3 shows a gradient pattern of HPLC used in Examples 2, 3 and 4. The axis of abscissa refers to ammonium sulfate concentration (M) and the axis of ordinate to time (min).

Gradient: The gradient between eluent A and eluent B is shown in FIG. 3.

Measuring procedure

A specimen having the same composition as that of the specimen 3 used in Example 1 was used as specimen 1, and a specimen having the same composition as that of the specimen 4 used in Example 1 was used as specimen 2. Each specimen was allowed to stand at 30° C. for 30 minutes and then 50 μl of the specimen was analyzed by HPLC.

Results

As a result of the analysis by HPLC, it was found that the POD-labeled anti-AFP-Fab' was eluted after 4.9 minutes, a complex of the POD-labeled anti-AFP-Fab' and AFP after 6.7 minutes, and a complex of the POD- labeled anti-AFP-Fab', the β-Gal-attached anti-AFP-Fab' and AFP after 9.7 minutes.

From these results, it can be seen that the employment of the modified affinity substance permits clearer separation of the POD-labeled anti-AFP-Fab' and the complex from each other.

EXAMPLE 3

Measurement of AFP (by use of iodine as separation-improving substance and a packing for hydrophobic chromatography).

Antibody solution 1

The same as the antibody solution 3 used in Example 1.

Antibody solutions 2

The same anti-AFP monoclonal antibody as used for the antibody solution 4 in Example 1 was iodinated by a conventional chloramine-T method [Japanese Biochemical Association "Seikagaku Jikken Koza (Biochemical Experiments) Vol. 16 (Hormone Vol. 1)" Tokyo Kagaku Dojin, pp. 117–180 and pp. 230–231, 1977]. Each of the iodinated anti-AFP monoclonal antibodies obtained by adjusting the iodination time to 5 seconds, 30 seconds or 2 minutes was added to 50 mM phosphate buffer (pH 7.5, containing 150 mM sodium chloride) to adjust the protein concentration to 50 nM, whereby antibody solution 2-1, antibody solution 2-2 and antibody solution 2-3 were obtained, respectively, Sample The same as the AFP sample solution used in Example 1.

Use conditions of HPLC

The same as in Example 2.

Measuring procedure

With 30 μl of antibody solution 1 and 30 μl of the AFP sample solution was mixed 30 μl of 50 mM phosphate buffer (pH 7.5, containing 150 mM sodium chloride), antibody solution 2-1, antibody solution 2-2 or antibody solution 2-3. After standing at 30° C. for 30 minutes, 50 μl of each of the thus obtained mixtures was analyzed by HPLC.

Results

As a result of the analysis by HPLC, it was found that the POD-labeled anti-AFP-Fab' was eluted after 4.9 minutes, and a complex A of the POD-labeled anti-AFP-Fab' and AFP after 6.7 minutes. It was also found that a complex of the POD-labeled anti-AFP-Fab', the iodinated anti-AFP-Fab' and AFP was eluted after 8.2 minutes (when antibody solution 2-1 was used), 9.5 minutes (when antibody solution 2-2 was used), or 9.9 minutes (when antibody solution 2-3 was used).

From the above results, it can be seen that the employment of the antibodies different in the amount of iodine attached (modified affinity substances) permits free control of the position of elution of complex of the POD-labeled anti-AFP-Fab' and AFP.

EXAMPLE 4

Measurement of AFP (by use of octylamine, phenylalanine tetramer (hereinafter abbreviated as Phe4), BMH or EMCS as separation-improving substance and a packing for hydrophobic chromatography).

Antibody solution 1

The same as the antibody solution 3 used in Example 1.

Antibody solution 2

Equimolar amounts of octylamine dissolved in 0.1M phosphate buffer [pH 7.0, containing 50% dimethylformamide (DMF)] and Sulfo-SMCC (mfd. by Pierce Chemical Co.) were reacted with each other by a conventional method. Then, Fab' (anti-AFP-Fab') [dissolved in 0.1M phosphate buffer (pH 7.0)] obtained by treating an anti- AFP monoclonal antibody different in epitope from the antibody used in antibody solution 1 by a conventional method was added to the reaction solution in an amount of 1/100 mole per mole of the octylamine. The resulting suspension was incubated at 30° C. for 30 minutes. By purification from the thus obtained reaction solution by a conventional method, octylamine-attached anti-AFP-Fab' was obtained. This product was added to 50 mM phosphate buffer (pH 7.5, containing 150 mM sodium chloride) to adjust the protein concentration to 50 nM, whereby antibody solution 2 was obtained.

Antibody solution 3

Phe4-attached AFP-Fab' was prepared by use of the same reagents and the same procedure as used for preparing antibody solution 2, except for using Phe4 peptide in place of octylamine. It was added to 50 mM phosphate buffer (pH 7.5, containing 150 mM sodium chloride) to adjust the protein concentration to 50 nM, whereby antibody solution 3 was obtained.

Antibody solution 4

The same anti-AFP-Fab' as used for preparing antibody solution 2 was reacted with BMH by a conventional method. N-acetyl-L-cysteine (AC) was added to the reaction solution in an amount of 100 moles per mole of BMH, followed by incubation at 30° C. for 30 minutes. By purification from the thus obtained reaction solution by a conventional method, AC-BMH-attached anti-AFP-Fab' was obtained. This product was added to 50 mM phosphate buffer (pH 7.5, containing 150 mM sodium chloride) to adjust the protein concentration to 50 nM, whereby antibody solution 4 was obtained.

Antibody solution 5

The same anti-AFP-Fab' as used for preparing antibody solution 2 was reacted with EMCS by a conventional method. Glycine was added to the reaction solution in an amount of 1,000 moles per mole of EMCS, followed by incubation at 30° C. for 30 minutes. By purification from the thus obtained reaction solution by a conventional method, glycine-EMCS-attached anti-AFP-Fab' was obtained. This product was added to 50 mM phosphate buffer (pH 7.5, containing 150 mM sodium chloride) to adjust the protein concentration to 50 nM, whereby antibody solution 5 was obtained.

Sample

The same as the AFP sample solution used in Example 1.

Use conditions of HPLC

The same as in Example 2.

Measuring procedure

With 30 μl of antibody solution 1 and 30 μl of the AFP sample solution was mixed 30 μl of 50 mM phosphate buffer (pH 7.5, containing 150 mM sodium chloride), antibody solution 2, antibody solution 3, antibody solution 4 or antibody solution 5. After standing at 30° C. for 30 minutes, 50 μl of each of the thus obtained mixtures was analyzed by HPLC.

Results

As a result of the analysis by HPLC, it was found that the POD-labeled anti-AFP-Fab' was eluted after 4.9 minutes, and a complex A of the POD-labeled anti-AFP-Fab' and AFP after 6.7 minutes. It was also found that a complex of the POD-labeled anti-AFP-Fab', AFP and each modified anti-AFP-Fab' (modified affinity substance) was eluted after 7.5 minutes (when the octylamine-attached anti-AFP-Fab' was used), 8.5 minutes (when the Phe4-attached anti-AFP-Fab' was used), 7.2 minutes (when the AC-BMH-attached anti-AFP-Fab' was used), or 7.1 minutes (when the glycine-EMCS-attached anti-AFP-Fab' was used).

From the above results, it can be seen that the position of elution of an objective complex can be freely controlled by changing the kind of the separation-improving substance.

EXAMPLE 5

Measurement of AFP (by use of a poly(aspartic acid) as separation-improving substance and a packing for anion-exchange chromatography).

Eluent A

As eluent A, 10 mM phosphate buffer (pH 7.5) was used.

Eluent B

As eluent B, 50 mM phosphate buffer (pH 7.5) containing 1M sodium chloride was used.

Substrate solution

A substrate solution was prepared by dissolving 4-methylumbelliferyl galactopyranoside in 50 mM phosphate buffer (pH 7.5) containing 20% DMF and 150 mM sodium chloride, to a concentration of 2.5 mM.

Antibody solution 1

Anti-AFP monoclonal antibody (available from Wako Pure Chemical Industries, Ltd.) was treated into Fab' by a conventional method. This Fab' was labeled with β-Gal by a conventional method and the thus obtained β-Gal-labeled anti-AFP-Fab' was added to 50 mM phosphate buffer (pH 7.5, containing 150 mM sodium chloride) to adjust the protein concentration to 4 nM, whereby antibody solution 1 was obtained.

Antibody solutions 2

Anti-AFP monoclonal antibody (available from Wako Pure Chemical Industries, Ltd.) which had been confirmed to be different in epitope from the monoclonal antibody used in antibody solution 1 was treated into Fab' by a conventional method. This Fab' was combined with a poly(arpartic acid) (average molecular weight: 6,165, 13,000 or 28,800, mfd. by Sigma Chemical Co.) by a conventional method using Sulfo-SMCC (mfd. by Pierce Chemical Co.), followed by purification by a conventional method. Thus, various poly(aspartic acid)-attached anti-AFP-Fab' materials were obtained. Each of them was added to 50 mM phosphate buffer (pH 7.5, containing 150 mM sodium chloride) to adjust the protein concentration to 50 nM, whereby antibody solutions 2 were obtained.

Sample

The same as the AFP sample solution used in Example 1.

Use conditions of HPLC

The outline of a system is given in FIG. 2.

Column: 0.46 φ×3.0 cm.

Packing: DEAE-MCI gel (a trade name, Mitsubishi Kasei Corp.)

Flow rate: eluents A+B; 1.0 ml/min, the substrate solution; 0.1 ml/min.

Reaction section: 0.025 φ×1,000 cm (maintained at 45° C.).

Detection: Fluorescence was measured at an excitation wavelength of 360 nm and an emission wavelength of 450 nm.

Figure 4:
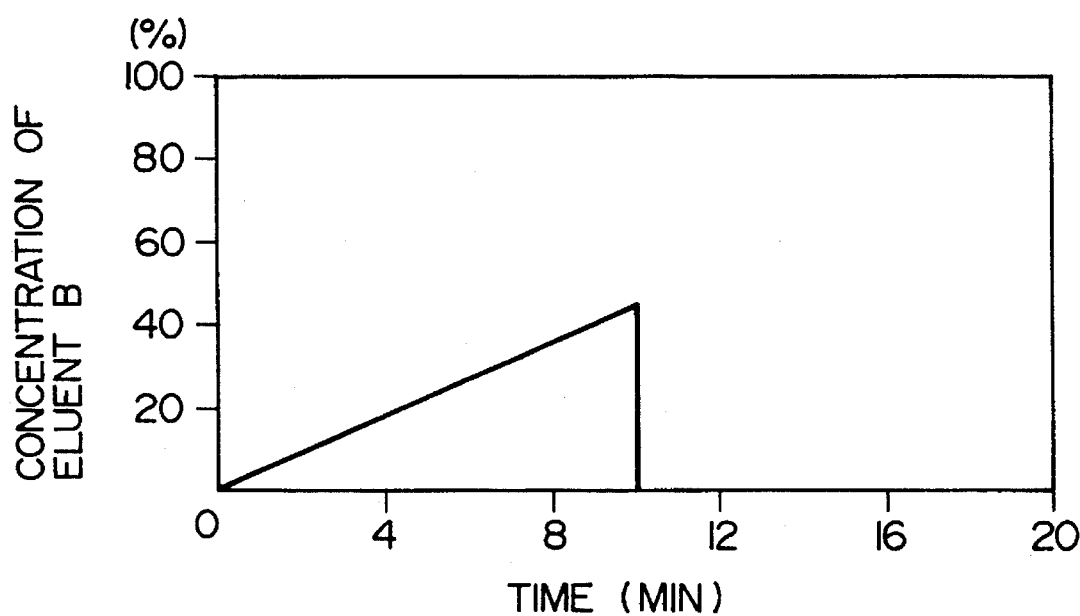
FIG. 4 shows a gradient pattern of HPLC used in Examples 5, 6, 7, 8 and 9. The axis of abscissa refers to the concentration (%) of eluent B and the axis of ordinate to time (min).

Gradient: The gradient between eluent A and eluent B is shown in FIG. 4.

Measuring procedure

With 30 μl of antibody solution 1 and 30 μl of the AFP sample solution was mixed 30 μl of 50 mM phosphate buffer (pH 7.5, containing 150 mM sodium chloride) or antibody solution 2 containing anti-AFP-Fab' having each poly(aspartic acid) attached thereto. After standing at 30° C. for 30 minutes, 50 μl of each of the thus obtained mixtures was analyzed by HPLC.

Results

As a result of the analysis by HPLC, it was found that the β-Gal-labeled anti-AFP-Fab' was eluted after 3.33 minutes, and a complex of the β-Gal-labeled anti-AFP-Fab' and AFP after 4.2 minutes. It was also found that a complex of the β-Gal-labeled anti-AFP-Fab', AFP and each poly(aspartic acid)-attached anti-AFP-Fab' (modified affinity substance) was eluted after 4.99 minutes, 7.90 minutes or 8.85 minutes when the average molecular weight of the poly(aspartic acid) attached was 6,165, 13,000 or 28,800, respectively.

From the above results, it can be seen that the position of elution of the complex can be freely controlled by changing the property of the separation-improving substance, i.e., the molecular weight of the poly(aspartic acid).

EXAMPLE 6

Figure 5A:
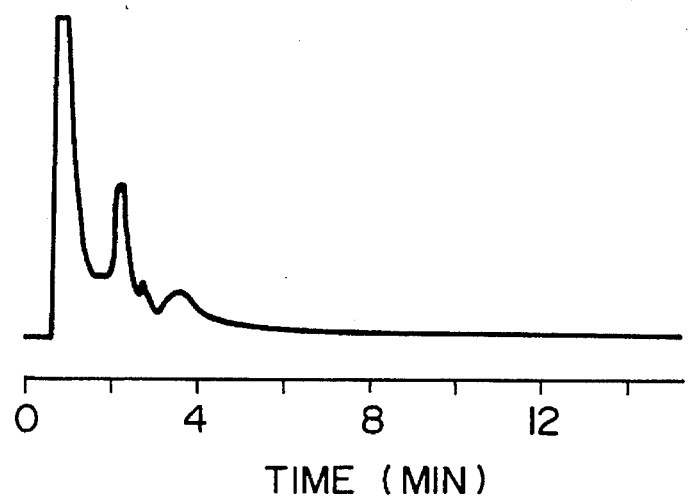
FIGS. 5A to 5C shows elution patterns of specimens which were obtained by HPLC in Example 6.
Figure 5B:
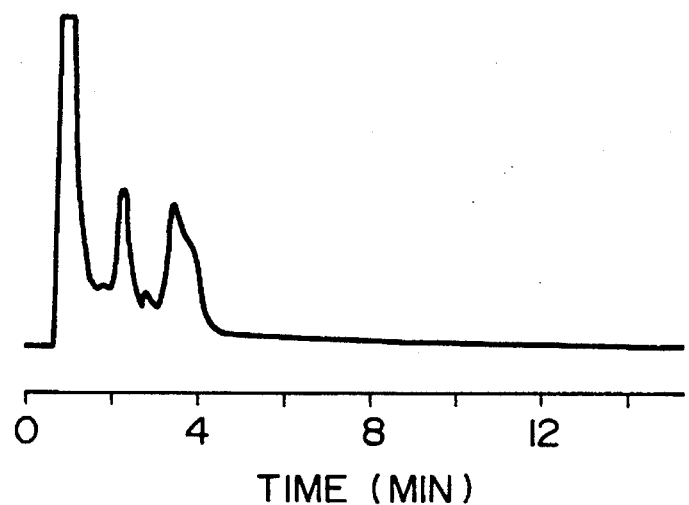
Figure 5C:
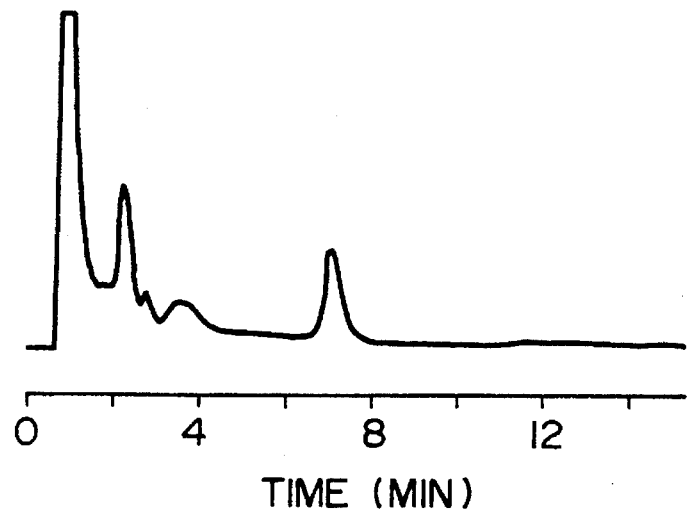

Investigation of avoidance of the influence of hemolysis in AFP measurement (in the case of using a poly(aspartic acid) as separation-improving substance and a packing for anion-exchange chromatography).
Eluent A
  The same as the eluent A used in Example 5.
Eluent B
  The same as the eluent B used in Example 5.
Substrate solution
  The same as the substrate solution used in Example 1.
Antibody solution 1
  The same as the antibody solution 3 used in Example 1.
Antibody solution 2
  Anti-AFP monoclonal antibody (available from Wako Pure Chemical Industries, Ltd.) which had been confirmed to be different in epitope from the monoclonal antibody used in antibody solution 1 was treated into Fab' by a conventional method. This Fab' was combined with a poly(arpartic acid) (average molecular weight: 13,000, mfd. by Sigma Chemical Co.) by a conventional method using Sulfo-SMCC (mfd. by Pierce Chemical Co.), followed by purification by a conventional method. Thus, anti-AFP-Fab' having the poly(aspartic acid) attached thereto was obtained. It was added to 50 mM phosphate buffer (pH 7.5, containing 150 mM sodium chloride) to adjust the protein concentration to 50 nM, whereby antibody solution 2 was obtained.
Hemolysate
  Hemolysate was prepared by diluting hemoglobin obtained from human erythrocytes with 50 mM phosphate buffer (pH 7.5, containing 150 mM sodium chloride) to 1,000 mg/dl.
Sample
  The same as the AFP sample solution used in Example 1.
Use conditions of HPLC
  The outline of a system is given in FIG. 2.
  Column: 0.46 φ×3.0 cm.
  Packing: Wakobeads DEAE gel (a trade name, Wako Pure Chemical Industries Ltd.).
  Flow rate: eluents A+B; 1.0 ml/min, the substrate solution; 0.1 ml/min.
  Reaction section: 0.025 φ×1,000 cm (maintained at 55° C.).
  Detection: Fluorescence was measured at an excitation wavelength of 320 nm and an emission wavelength of 404 nm.
  Gradient: The gradient between eluent A and eluent B is shown in FIG. 4.
Measuring procedure
  With 30 μl of antibody solution 1 and 10 μl of the AFP sample solution was mixed 30 μl of 50 mM phosphate buffer (pH 7.5, containing 150 mM sodium chloride) or antibody solution 2. After standing at 30° C. for 30 minutes, 50 μl of each of the thus obtained mixtures was analyzed by HPLC.
Results
  FIGS. 5A to 5C show elution patterns obtained. FIG. 5A shows an elution pattern obtained by analyzing a dilution prepared by diluting the hemolysate such that the concentration of hemolysate was 1/10, the dilution being made with 50 mM of phosphate buffer (pH 7.5, containing 150 mM sodium chloride). FIG. 5B shows an elution pattern obtained by analyzing a mixture of antibody solution 1, the AFP sample solution, the hemolysate and the phosphate buffer. FIG. 5C shows an elution pattern obtained by analyzing a mixture of antibody solution 1, the AFP sample solution, the hemolysate and antibody solution 2.

As is clear from FIG. 5A, components of the hemolysate appeared as a plurality of peaks after 0.5 to 5.5 minutes. On the other hand, it can be seen that the POD-labeled anti-AFP-Fab' was eluted after 1.10 minutes, a complex of the POD-labeled anti-AFP-Fab' and AFP after 3.25 minutes, and a complex of the POD-labeled anti-AFP-Fab', the poly(aspartic acid)-attached anti-AFP-Fab' and AFP after 7.20 minutes.

The above results indicate the following. The utilization of the separating process of this invention permits elution of the complex at a position at which the measurement is not affected by hemolysis at all. In other words, the utilization of the separating process of this invention makes it possible to measure an analyte without any influence of the components of hemolysate in a sample during the measurement. Therefore, a higher precision of measurement than before can be attained.

EXAMPLE 7

Separation and measurement of hCG's different in sugar chain structure (by use of a poly(aspartic acid) as separation-improving substance and a packing for anion-exchange chromatography).
Antibody solution
  The same as the antibody solution 1 used in Example 1.
Lectin solution 1
  Lectin solution 1 was prepared by adding Datura stramonium lectin (Datura lectin) (available from Wako Pure Chemical Industries, Ltd.) to 50 mM tris(hydroxymethyl)aminomethane (hereinafter "Tris")-hydrochloric acid buffer (pH 7.5, containing 150 mM sodium chloride and 1 mM calcium chloride) to adjust the protein concentration to 1 mg/ml.
Lectin solution 2
  The same Datura lectin as used for preparing lectin solution 1 and a poly(aspartic acid) (average molecular weight: 28,800) were made into a poly(aspartic acid)-attached Datura lectin by a conventional method using disuccinimidyl suberate (mfd. by Pierce Chemical Co.). This product was added to 50 mM Tris-hydrochloric acid buffer (pH 7.5, containing 150 mM sodium chloride and 1 mM calcium chloride) to adjust the protein concentration to 1 mg/ml, whereby lectin solution 2 was obtained.
hCG sample solution
  A hCG sample solution was prepared by adding hCG derived from human choriocarcinoma (available from Wako Pure Chemical Industries, Ltd.) to 50 mM Tris-hydrochloric acid buffer (pH 7.5, containing 150 mM sodium chloride and 1 mM calcium chloride) to adjust the hCG concentration to 250 mIU/ml.
Use conditions of HPLC
  The same as in Example 6.
Measuring procedure
  With 10 μl of the hCG sample solution and 20 μl of the antibody solution was mixed 70 μl of lectin solution 1 or lectin solution 2. After standing at 30° C. for 30 minutes, 50 μl of each of the thus obtained mixtures was analyzed by HPLC.

Results

As a result of the analysis by HPLC, it was found that the POD-labeled anti-hCG-α chain-Fab' was eluted after 1.10 minutes, a complex of the POD-labeled anti-hCG-α chain-Fab' and hCG after 3.50 minutes, a complex of the POD-labeled anti-hCG-α chain-Fab', hCG and Datura lectin after 3.82 minutes, and a complex of the POD-labeled anti-hCG-α chain-Fab', hCG and the poly(aspartic acid)-attached Datura lectin after 7.9 minutes.

From the above results, it can be seen that the employment of the poly(aspartic acid)-attached Datura lectin permits clearer separation of the lectin-attached complex from the lectin-unattached complex, namely, the employment makes it possible to measure the amount of hCG having a specific sugar chain among all hCG's with higher precision.

EXAMPLE 8

Measurement of thyroxine ($T_4$) (by use of a poly(glutamic acid) as separation-improving substance and a packing for anion-exchange chromatography).

Eluent A

As eluent A, 20 mM Tris-hydrochloric acid buffer (pH 8.0) was used.

Eluent B

As eluent B, 20 mM Tris-hydrochloric acid buffer (pH 8.0) containing 1M sodium chloride was used.

Substrate solution

In 80 ml of eluent A was dissolved 1.66 g of 3-(p-hydroxyphenyl)-propionic acid, and the resulting solution was adjusted to pH 8.0 with 1N sodium hydroxide, followed by making up the total volume of 100 ml with eluent A. A 30% aqueous hydrogen peroxide solution was diluted with the resulting solution, whereby a 20 mM solution of $H_2O_2$ was prepared as a substrate solution.

Antibody solution 1

Anti-$T_4$ monoclonal antibody (available from Wako Pure Chemical Industries, Ltd.) was treated into Fab' by a conventional method. This Fab' was labeled with horseradish peroxidase (POD) by a conventional method and the thus obtained POD-labeled anti-$T_4$-Fab' was added to 20 mM Tris-hydrochloric acid buffer (pH 8.0) to adjust the protein concentration to 3 nM, whereby antibody solution 1 was obtained.

Antibody solution 2

Anti-POD monoclonal antibody (available from Wako Pure Chemical Industries, Ltd.) was treated into Fab' by a conventional method. This Fab' was combined with a poly(glutamic acid) (average molecular weight: 95,100, mfd. by Sigma Chemical Co.) by a conventional method using Sulfo-SMCC. The thus obtained poly(glutamic acid)-attached anti-POD-Fab' was added to 20 mM Tris-hydrochloric acid buffer (pH 8.0) to adjust the protein concentration to 50 nM, whereby antibody solution 2 was obtained.

The POD monoclonal antibody used in this case had a property of binding to POD but not inhibiting its enzyme activity.

$T_4$ sample solution

A $T_4$ sample solution was prepared by adding commercial L-thyroxine (available from Sigma Chemical Co.) to 20 mM Tris-hydrochloric acid buffer (pH 8.0) to adjust the protein concentration to 10 nM.

Use conditions of HPLC

The outline of a system is given in FIG. 2.

Column: 0.46 φ×3.0 cm.

Packing: Wakobeads DEAE gel (a trade name, Wako Pure Chemical Industries Ltd.).

Flow rate: eluents A+B; 1.0 ml/min, the substrate solution; 0.1 ml/min.

Reaction section: 0.025 φ×1,000 cm (maintained at 55° C.).

Detection: Fluorescence was measured at an excitation wavelength of 320 nm and an emission wavelength of 404 nm.

Gradient: The gradient between eluent A and eluent B is shown in FIG. 4.

Measuring procedure

A mixture of 30 μl of the $T_4$ sample solution, 30 μl of antibody solution 1 and 30 μl of 20 mM Tris-hydrochloric acid buffer (pH 8.0) was used as specimen 1. A mixture of 30 μl of the $T_4$ sample solution, 30 μl of antibody solution 1 and 30 μl of antibody solution 2 was used as specimen 2. After standing at 30° C. for 30 minutes, 50 μl of each specimen was analyzed by HPLC.

Results

As a result of the analysis by HPLC, it was found that the POD-labeled anti-$T_4$-Fab' was eluted after 3.3 minutes, a complex of the POD-labeled anti-$T_4$-Fab' and $T_4$ after 2.3 minutes, a complex of the POD-labeled anti-$T_4$-Fab' and the poly(glutamic acid)-attached anti-POD-Fab' after 8.9 minutes, and a complex of the POD-labeled anti-$T_4$-Fab', the poly(glutamic acid)-attached anti-POD-Fab' and $T_4$ after 7.4 minutes.

From the above results, it can be seen that the employment of the poly(glutamic acid)-attached anti-POD-Fab' makes it possible to change the positions of elution of the POD-labeled anti-$T_4$-Fab' and the complex of the POD-labeled anti-$T_4$-Fab' and $T_4$, namely, the employment permits clearer separation of the POD-labeled anti-$T_4$-Fab' and the complex of the POD-labeled anti-$T_4$-Fab' and $T_4$ from each other.

Investigation of avoidance of the influence of hemolysis in thyroxine measurement (by use of poly(glutamic acid) as separation improving substance and packing substance for anion-exchange chromatography.

Labeled antigen

A labeled antigen solution was prepared by dissolving POD-labeled $T_4$ prepared by a conventional method (NAKANE method: Nakane, P. K. and Kawaoi, A., J. Histochem. Cytochem., vol. 22, 1084–1091, 1974), in 20 mM Tris-hydrochloric acid buffer (pH 8.0) to adjust its concentration to 10 nm.

Antibody solution 1

Anti-$T_4$ monoclonal antibody (mfd. by Wako Pure Chemical Industries, Ltd.) was treated into Fab' by a conventional method. N-ethylmaleimide was added to the Fab' in an amount of 20 moles per mole of the Fab', and the resulting mixture was allowed to stand at 37° C. for 60 minutes, whereby the reaction was carried out. The reaction product was purified by a conventional method to obtain N-ethylsuccinimide-modified Fab', which was added to 20 mM Tris-hydrochloric acid buffer (pH 8.0) to adjust the protein concentration to 2 nM, whereby antibody solution 1 was obtained.

Antibody solution 2

The same as the antibody solution 2 used in Example 8.

$T_4$ sample solution

The same as the $T_4$ sample solution used in Example 8.

Hemolysate

The same as the hemolysate used in Example 6.

Use conditions of HPLC

The same as in Example 8.

Measuring procedure

Specimens 1 to 3 having the compositions shown in Table 2 were prepared. Each specimen was allowed to stand at 30°

C. for 30 minutes and then 50 µl of the specimen was analyzed by HPLC.

TABLE 2

|  | Specimen | | |
| --- | --- | --- | --- |
|  | 1 | 2 | 3 |
| T4 sample solution | 20 ul | 20 ul | 20 ul |
| Labeled antigen | 20 ul | 20 ul | 20 ul |
| Antibody solution 1 | 30 ul | 30 ul | 30 ul |
| Antibody solution 2 | — | 20 ul | 20 ul |
| Hemolysate | — | — | 10 ul |
| Tris buffer *1 | 20 ul | — | — |
| Phosphate buffer *2 | 10 ul | 10 ul | — |

*1: 20 mM Tris-HCl buffer (pH 80)
*2: 50 mM phosphate buffer (pH 75 containing 150 mM NaCl)

Results

As a result of the analysis by HPLC, it was found that the POD-labeled $T_4$ was eluted after 2.6 minutes, a complex of the POD-labeled $T_4$ and the N-ethylsuccinimide-modified Fab' after 3.5 minutes, and a complex of the POD-labeled $T_4$ and the poly(glutamic acid)-attached anti-POD-Fab' after 8.3 minutes, and a complex of the POD-labeled $T_4$, the N-ethylsuccinimide-modified Fab' and the poly(glutamic acid)-attached anti-POD-Fab' after 9.1 minutes. On the other hand, it was found that components of the hemolysate were eluted as a plurality of peaks after 0.5 to 5.5 minutes as in Example 6.

The above results indicate the following. The utilization of the separating process of this invention permits elution of the complex at a position at which the measurement is not affected by hemolysis at all. In other words, the utilization of the separating process of this invention makes it possible to measure an analyte without any influence of the components of hemolysate in a sample during the measurement. Therefore, a higher precision of measurement than before can be attained.

As described above, this invention provides a measuring process in which a complex formed by the interaction between one or more analytes to be measured and an affinity substance therefor is separated from other substances such as free affinity substance (or free analyte(s)) and the like by using a high pressure liquid chromatography, said process being effective in that the position of elution of said complex in the high pressure liquid chromatography can be freely changed by changing properties of the complex freely by attaching a separation-improving substance to the complex. Moreover, said measuring process is markedly effective in that when a trace component in a sample derived from a living body, such as serum is measured by utilizing the separating process of this invention, the measuring process makes it possible to carry out the measurement more easily in a much shorter time with higher precision as compared with conventional measuring processes according to EIA, RIA or the like.

What is claimed is:

1. A process for separating a complex from free substances existing therewith which tend to affect the detection of the complex which comprises
    combining a complex of one or more analytes to be measured and an affinity substance A having affinity for the analytes, with a modified affinity substance B having affinity for the complex, said affinity substance B being modified by attachment to a separation-improving substance which when attached to the complex via affinity substance B can change a property of the complex for improving separation of the complex from free affinity substance A and the free substances, and
    separating the complex combined with the modified affinity substance B from free affinity substance A or the free substances by a high pressure liquid chromatography on the basis of properties of the separation-improving substance.

2. A process according to claim 1, wherein the separation-improving substance is a protein, peptide, synthetic high-molecular weight compound, poly(amino acid), halogen atom, alkyl chain, fatty acid or a chemical substance which has a reactive group capable of binding to an affinity substance B, said affinity substance B having affinity for the complex comprising one or more analytes and said affinity substance A, and wherein the chemical substance also has hydrophobic or charged groups.

3. A process according to claim 1, wherein the separation-improving substance is a protein, a synthetic high-molecular weight compound or a poly(amino acid), and wherein the high pressure liquid chromatography is conducted using a column packed with a packing for gel filtration.

4. A process according to claim 1, wherein the separation-improving substance is a protein, peptide, poly(amino acid), alkyl chain, halogen atom, fatty acid or a chemical substance which has a reactive group capable of binding to an affinity substance B, said affinity substance B having affinity for the complex comprising one or more analytes and the affinity substance A, wherein the chemical substance also has one or more hydrophobic groups, and wherein the high pressure liquid chromatography is conducted using a column packed for hydrophobic chromatography.

5. A process according to claim 1, wherein the separation-improving substance is a synthetic high-molecular weight compound, a protein, a poly(amino acid), a fatty acid, a peptide or a chemical substance which has a reactive group capable of binding to an affinity substance B, said affinity substance B having affinity for the complex comprising one or more analytes and the affinity substance A wherein the chemical substance also has one or more charged groups, and wherein the high pressure liquid chromatography is conducted using a column packed for ion-exchange chromatography.

6. A process for measuring one or more analytes which comprises:
    obtaining a complex of one or more analytes to be measured and a labelled affinity substance A which has affinity for said analyte(s) and is labeled with a detectable labeling substance by the reaction of the one or more analytes and the labeled affinity substance A,
    attaching an affinity substance B having affinity for the complex or the labeling substance and modified by attachment to a separation-improving substance which when attached to the complex via affinity substance B can change a property of the complex, to the complex
    separating the complex having the modified affinity substance B attached thereto from free labeled affinity substance A by high pressure liquid chromatography on the basis of properties of the separation-improving substance,
    measuring the amount of the complex or the free labeled affinity substance A, and
    determining the amount of the one or more analytes.

7. A process according to claim 6, wherein the high pressure liquid chromatography is conducted using a column packed with a packing for ion-exchange chromatography.

8. A process for measuring an analyte which comprises reacting a sample derived from a living body suspected of containing the analyte to be measured with analyte labeled with a detectable labeling substance, an affinity substance A having affinity for the analyte and an affinity substance B modified by attachment to a separation-improving substance capable of changing a property of a complex to be formed when attached thereto via affinity substance B said affinity substance B being capable of binding to a complex of the analyte and the affinity substance A to form (a) a complex of the analyte, the affinity substance A and the modified affinity substance B, and (b) a labeled complex of the labeled analyte, the affinity substance A and the modified affinity substance B, separating the labeled complex (b) from the labeled analyte by high pressure liquid chromatography on the basis of properties of the separation-improving substance, determining the amount of the detectable substance contained in the separated labeled complex, and determining the amount of the analyte.

9. A process according to claim 8, wherein the high pressure liquid chromatography is conducted using a column packed with a packing for ion-exchange chromatography.

10. A process for measuring two or more analytes having the same action and the same detectable chemical characteristics which comprises reacting a sample derived from a living body containing analytes to be measured with 1) an affinity substance A having a property of binding specifically to at least one of the analytes but not to at least one of the other analytes and 2) an affinity substance B modified by attachment to a separation-improving substance, wherein said affinity substance B is capable of binding to a complex of analytes and the affinity substance A to form a complex of the specific analytes, the affinity substance A and the modified affinity substance B, said separation-improving substance being capable of changing a property of the complex when attached thereto via affinity substance B, separating the complex of the specific analytes, the affinity substance A and the modified affinity substance B from free analytes by high pressure liquid chromatography, on the basis of properties of the separation-improving substance, determining the amount of the analytes contained in the thus separated complex or the amount of free analytes, or both, on the basis of the same detectable chemical characteristics of the analytes, and determining the amount of the analytes in the sample.

11. A process according to claim 10, wherein the high pressure liquid chromatography is conducted using a column packed with a packing for ion-exchange chromatography.

12. A process for measuring two or more analytes having the same action, or having different actions in spite of their similar structures, which comprises reacting a sample derived from a living body containing analytes to be measured with an affinity substance A having affinity for all the analytes and labeled with a detectable substance and an affinity substance B modified by attachment to a separation-improving substance, wherein said affinity substance B has affinity for at least one specific analyte of the analytes to be measured and said separation-improving substance is capable of changing properties of a complex of analytes, when attached thereto via affinity substance B to form (a) a complex of the analytes and the affinity substance A and (b) a complex of the specific analytes, the affinity substance A and the modified affinity substance B, separating the complex (a), the complex (b) and free affinity substance A from one another by high pressure liquid chromatography on the basis of properties of the separation-improving substance, determining the amount of the detectable substance contained in the separated complex (a) or the amount of the detectable substance contained in the separated complex (b), or both, on the basis of properties of the detectable substance, and determining the amount of any of the analytes in the sample.

13. A process according to claim 12, wherein the high pressure liquid chromatography is conducted using a column packed with a packing for ion-exchange chromatography.

* * * * *